(12) United States Patent
Jager et al.

(10) Patent No.: US 6,649,149 B2
(45) Date of Patent: Nov. 18, 2003

(54) TANNING PREPARATION FOR THE SKIN

(75) Inventors: Leo Anton Jager, Tiel (NL); Lukas Jan Jager, Tiel (NL); Edward Philip Jager, Teil (NL); Hans Marcel Brand, Nieuwerkerk aan de Ijssel (NL)

(73) Assignee: Dija Zeist B.V., Tiel (NL)

( * ) Notice: Subject to any disclaimer, the term of this patent is extended or adjusted under 35 U.S.C. 154(b) by 0 days.

(21) Appl. No.: 10/218,037

(22) Filed: Aug. 14, 2002

(65) Prior Publication Data

US 2003/0118527 A1 Jun. 26, 2003

Related U.S. Application Data

(63) Continuation of application No. PCT/NL01/00122, filed on Feb. 14, 2001.

(30) Foreign Application Priority Data

Feb. 15, 2000 (NL) .............................................. 1014389

(51) Int. Cl.$^7$ .......................... A61K 7/42; A61K 7/44; A61K 7/00
(52) U.S. Cl. .......................... 424/59; 424/60; 424/400; 424/401; 514/937; 514/938
(58) Field of Search ............................ 424/59, 60, 400, 424/401; 514/937, 938

(56) References Cited

U.S. PATENT DOCUMENTS

| 5,372,805 A | 12/1994 | Finkel et al. |
| 5,756,108 A | 5/1998 | Ribier et al. |
| 5,834,013 A | 11/1998 | Ribier et al. |

FOREIGN PATENT DOCUMENTS

| DE | 3836849 | 6/1989 |
| GB | 2213376 | 8/1989 |
| GB | 2 304 573 | 3/1997 |

*Primary Examiner*—Shelley A. Dodson
(74) *Attorney, Agent, or Firm*—Browdy and Neimark, P.L.L.C.

(57) ABSTRACT

The invention relates to a tanning preparation for the skin comprising at least one tyrosine derivative of formula 1, where $R_1$=—H, —(CH2)x-CH3, x being an integer from 1 to 20, $R_2$=CH3CO—, CH3—(CH2)yCO—, y being an integer from 1 to 20, and an activator consisting of an aliphatic polyol having at least 10 C atoms in the molecule. The aliphatic polyol preferably consists of a hexadecanetriol, in particular phytantriol. Expediently, the tanning preparation is a gel, lotion, cream, foam, spray or emulsion. The invention further relates to a controlled release tanning preparation for the skin

10 Claims, 2 Drawing Sheets

TANNING PREPARATION FOR THE SKIN

CROSS-REFERENCE TO RELATED APPLICATION

Figure 1:
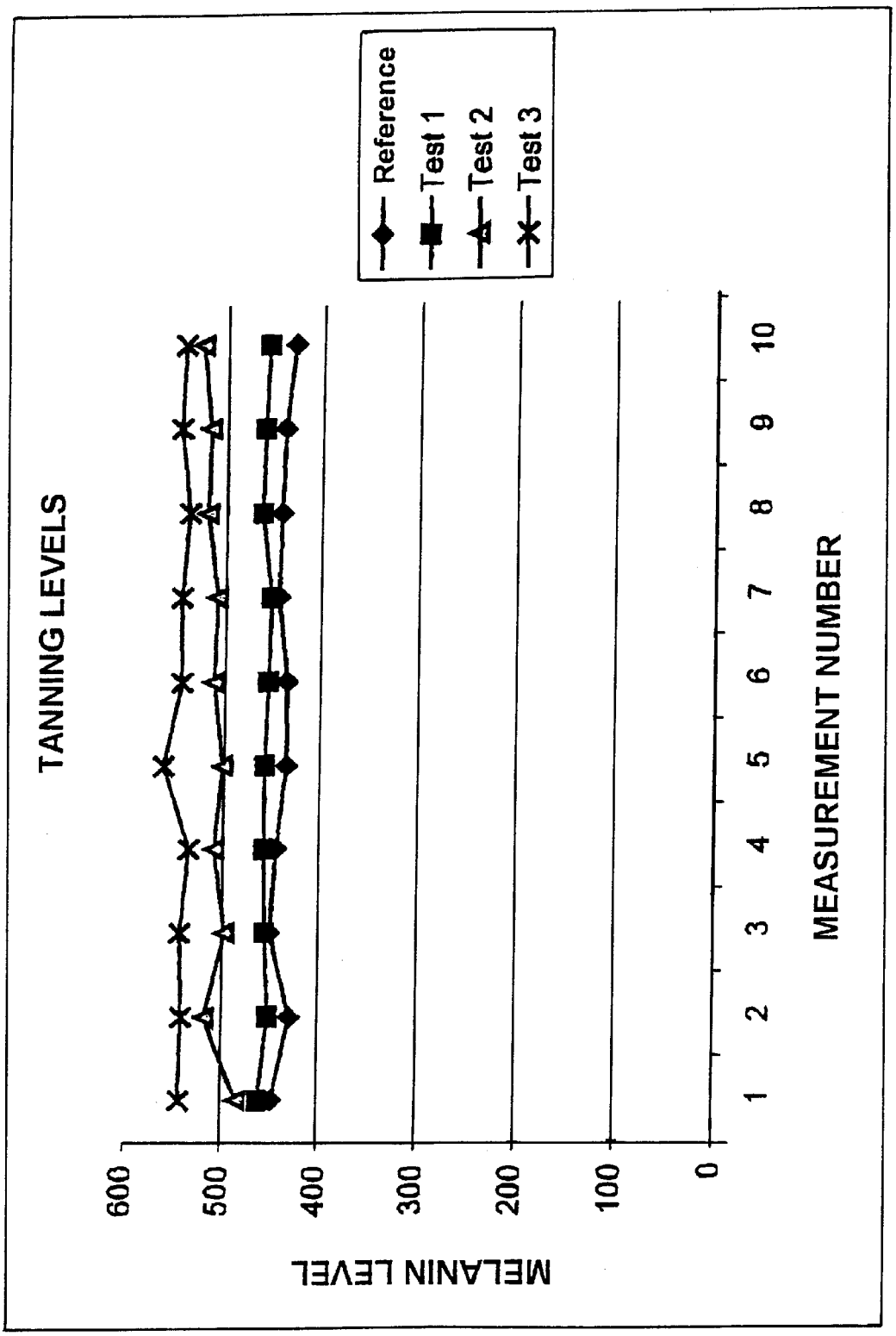

This is a continuation application of PCT/NL01/00122 filed Feb. 14, 2001, which PCT application claims priority of Dutch patent applicaton numner 1014389 filed Feb. 15, 2000, both herin incorporated by reference.

BACKGROUND OF THE INVENTION

The invention relates to a tanning preparation for the skin comprising at least one tyrosine derivative of formula 1

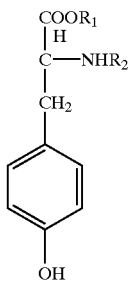

where
R$^1$=—H,— (CH$_2$) X—CH$_3$, x being an integer from 1 to 20,
R$^2$=CH$_3$CO—, CH$_3$— (CH$_2$) yCO—, y being an integer from 1 to 20, and an activator.

A preparation of this type is disclosed by DE-C-3 732 154. As this publication states, the skin pigment melanin is formed in the skin from the amino acid tyrosine. This reaction takes place under the influence of light, heat and oxygen, with the aid of the enzyme tyrosinase.

On the basis of this known biological process it was found that certain tyrosine derivatives, in combination with an activator as a substitute for the expensive and chemically unstable enzyme, may lead to the desired tanning of the skin, if used as a sunburn preparation. As an activator, this known preparation comprises an adenosine compound such as an ester or a salt of adenosine mono-, di- or triphosphoric acid.

Adenosine di- and triphosphate are known to be involved in various enzymatic reactions in the body, in particular in processes requiring energy such as the oxidation of sugars, proteins and fats.

DISCLOSURE OF THE INVENTION

Surprisingly, a tanning preparation has now been found for the skin wherein the activator used is not a substance which naturally occurs in the body and has an enzymatic reaction, but instead a compound which preferably has humectant activity.

The invention therefore relates, in a first embodiment, to a tanning preparation of the type mentioned at the outset, wherein the activator consists of an aliphatic polyol having at least 10 C atoms in the molecule.

Preferably, the aliphatic polyol consists of a hexadecanetriol, in particular phytantriol.

Phytantriol, or 3,7,11,15-tetramethyl-1,2,3-hexadecanetriol, is a compound which improves the moisture retention capability of the skin and of hair and-is therefore used in shampoos and hair conditioners; in this context, the Japanese patent application Kokai No JP-A2-61,236,737 can be mentioned.

It has now been found that an aliphatic polyol, and in particular phytantriol, improves the deposition of a tyrosine derivative as specified hereinabove on and in the skin, thereby allowing rapid and persistent, natural tanning of the skin to be achieved. Such an effect is rather surprising, all the more since only very small amounts of aliphatic polyol, in particular phytantriol, need be present in the tanning preparation.

Preferably, the tanning preparation according to the invention merely contains at least 0.01 wt % of phytantriol, it being noted in this context that even with this very small amount of phytantriol, rapid tanning of the skin is achieved.

Tyrosine derivatives which are particularly suitable for use in a tanning preparation according to the invention are N-acetyltyrosine; N-acetyltyrosine ethyl ester; N-myristoyltyrosine; N-myristoyltyrosine-myristylester; N-palmitoyltyrosine; N-palmitoyltyrosine-palmityl ester; N-stearoyltyrosine and N-stearoyltyrosine stearyl ester.

According to another expedient embodiment of a preparation according to the invention, the preparation further comprises riboflavin.

Riboflavin or vitamin B2 is 7,8-dimethyl-10 (D-1'-ribityl)-isoalloxazine and is a compound which in the body is converted into two coenzymes, viz. FMN and FAD, which are involved in numerous oxidation-reduction processes.

It should be noted that the use of riboflavin as an activator in a sunburn preparation comprising a tyrosine derivative is known per se from CH 642 537. An activator consisting of an aliphatic polyol, as described hereinabove, is not mentioned in this publication, however. The use of riboflavin according to the invention is optional, moreover, rather than mandatory as in CH 642 537.

According to yet another expedient embodiment of a preparation according to the invention, this preparation further comprises a W filter. The UV filter used can be any of the compounds suitable for this purpose in the customary quantities without any limitation.

The tanning preparation according to the invention can further be in the form of a gel, lotion, cream, foam, spray based on water and/or an aqueous alcohol and/or an aqueous glycol, or of an emulsion of the type O/W, W/O, O/W/O, etc.

Used as a solvent for aqueous solutions is, for example, water, aqueous ethanol, aqueous isopropanol, aqueous glycols or a mixture thereof. By adding a suitable emulsifier it is possible to form an emulsion or a gel, while an aerosol or a foam can be formed with the aid of a suitable propellant.

It should be noted that the tyrosine derivatives carrying relatively long-chain substituents are preferably dissolved in an oil. Examples of these are mineral oils such as paraffin oil, vegetable oil such as olive oil and animal oil such as squalene. Waxes such as beeswax and fat-dissolving glycols and polyglycols can also be used, however.

In addition, a tanning preparation according to the invention can comprise customary adjuvants, depending on the desired form of the preparation, such as surfactants, swelling agents or thickeners, emulsifiers and hydrolysed vegetable protein such as hydrolysed soya protein and hydrolysed wheat protein.

The invention further relates to a method of preparing a tanning preparation as described hereinabove, wherein a mixture is formed which comprises
5–15 wt % of N-acetyl-L-tyrosine,
0.5–5 wt % of phytantriol,
15–25 wt % of butylene glycol,
1–5 wt % of hydrolysed vegetable protein, 0.1–5 wt % of polysorbate-20, 0–5 wt % of riboflavin, remainder: water/alcohol, and this mixture is taken up in an amount of from 1 to 10%, preferably 5%, in a pharmacologically acceptable base to form a preparation for topical application.

According to a preferred embodiment of a method of preparing a tanning preparation according to the invention, a mixture is formed which comprises 10 wt % of N-acetyl-L-tyrosine, 20 wt % of butylene glycol, 2 wt % of phytantriol, 3 wt % of hydrolysed soya protein, 3 wt % of polysorbate-20, 1 wt % of riboflavin, remainder: water, and this mixture is taken up in an amount of 5%, in a water/ethanol/glycol mixture to form a lotion.

According to another embodiment, the present invention relates to a controlled release tanning preparation.

With respect to the phenomenon of controlled release preparations the following explanation is given.

Stable emulsions, produced for application in food, pharmacy, personal care and cosmetics, lacquers and coatings, paper products, etc., are characterized by the presence of a nematic, liquid crystalline structure.

The rationale for the existence of thermodynamically stable liquid crystalline (LC) structures is dependant on the temperature, and it is a boundary condition for stable emulsions that these LC structures are manifest in the temperature range of storage and application of the particular product.

Griffin defined in the 50's the famous HLB concept whereby it was stated that stable emulsions can be prepared when the HLB value was –10. Israelachvili et. al. (1975) showed that an optimum liquid crystalline phase exists in the case the emulsifier/emulsifier combination had an HLB value –10.

The nematic liquid crystalline structures reside in the continuous phase of emulsions. These are organised in double layers whereby the theme "like-dissolves-like" is applicable.

The double layers, relative to the continuous phase applicable, may be organised as:

 (1)

 (2)

whereby H represents the hydrophilic (water-loving) part hydrophlllc the surface active agent, and <<L>> represents the lipophilic (oil-loving) part of the surface active agent. Thus, structure (1) will reside in the water phase and is characteristic for Oil-in-Water (O/W) emulsions. Structure (2) will reside in the oil phase and is therefore characteristic for Water-in-Oil (W/O) emulsions.

The LC structure is present in the form of a sponge structure. A number of parameters are determining the characteristics of the frequently called "the fourth phase".

These are:

1. Mechanical strength of the LC phase.
2. Abundance of the LC phase.
3. The possibility of existence of the LC phase in the temperature range that is usually for personal care and cosmetic products (–10 C to +50 C).
4. The possibility to make the liquid crystalline phase in a temperature range of –10 C to +90 C.
5. oil droplet size distribution/particle size distribution of the dispersed phase.

Especially the mechanical strength of the LC is an important parameter for the cosmetic application of active ingredients relative to the bio-availability of these active ingredients. In traditional emulsion systems the LC structures are quickly deteriorated because of the influence of shear applied during rubbing in, the influence of electrolytes, the activity of enzymes present on the skin and because of the presence of liquid crystalline structures relative to the naturally occurring sebum (the sebum also exhibits liquid crystalline properties, and easily dissolves the LC structures present in cosmetic emulsions).

Also, currently commercially available cosmetic emulsions are mostly stabilised by manipulation of the rheological properties by means of inappropriate use of rheological additives, ignoring the challenge and possibilities of the application of liquid crystalline behaviour.

As a consequence the behaviour of traditional emulsions applied for personal care and cosmetic products is such that the bio-availability of active ingredients is almost immediate. Usually this is not very appreciated as the active period of the active principles is therefore short and the largest part of the active principles is processed "unused".

Active principles could be considered to be moisturisers/humectants, oil/water-soluble W-filters, flavonoids, saponines, alkaloids, terpenoids, vitamins, 2hydroxy carboxylic acids (AHA's), insect repellents, amino acid biovectors, (poly)-saccharides, etc.

It is possible to increase the mechanical strength of the liquid crystalline structures on the skin during and after application, while maintaining the required sensorial properties of personal care and cosmetic emulsions. It has been found that this can be done using appropriate hydrocolloids such as naturals gums (such as xanthan gum, karaya gum, guar gum, gum ghatti, gum Arabic, etc.), cellulose derivatives (such as methylcellulose, hydroxyethyl cellulose, hydroxypropyl cellulose, hydroxypropyl methylcellulose, etc.), synthetic hydrophilic products such as homo-and co-polymers of acrylic acid, methacrylic acid, crotonic acid, etc, natural clays such as hectorites, bentonites, montmorrilonites, and others.

The mechanical strength of the LC structures can easily be measured in terms of Theological parameters such as yield stress value, visco-elastic behaviour and flow patterns.

In this way it is possible to produce emulsions that do not show degradation on the time scale required for cosmetic application. While doing so the bio-availability of active ingredients is than turned to the other side of the spectrum and consequently the bio-availability is reduced to levels where the activity is at least insufficient and frequently not noticeable anymore.

Although Applicant does not wish to be bound by any theory, it is assumed that this can be obviated by the incorporation in the strengthened LC of structure molecules that are "recognised" by the skin, in particular the sebum and the first sub-cutaneous membranes composed of lecithin and similar phospholipids. Cholesterol is produced on the skin via bio-conversion of squalene and is incorporated in those lecithin membranes. It is connected to "siphon-molecules", identified as glycolipids and/or glycoproteins. To allow small molecules to pass the membrane the cholesterol molecule is temporarily pulled out of the lecithin double layer by means of a glycolipid or glycoprotein, under the influence of e.g. osmotic pressure. As soon as transport of the desired molecules (water, small carbohydrates, carbon dioxide, metal ions, etc.) has taken place the cholesterol molecule is put back in the lecithin membrane.

By building in cholesterol in the double layer composed of surface active agents the same mechanism can be used for a controlled release mechanism of active substances. Using the same receptors cholesterol can be pulled out of the double layer and make the contents of the liquid crystalline cavity available to the skin. This mechanism may coincide with enzymatic degradation of the liquid crystalline sponge structure. The naturally occuring receptors for cholesterol are thus used to enable controlled release.

A number of systems composed of surface active agents that for LC structures in either hydrophilic or lipophilic media were tested on this mechanism, to be identified as:

a. $\begin{cases} Steareth-2a. \\ Steareth-21 \end{cases}$ b. $\begin{cases} Glyceryl\ Stearate \\ Potassium\ Stearate \end{cases}$ c. $\begin{cases} Methylglucose\ Sesquistearate \\ PEG-20\ Methylglucose\ Sesquistearate \end{cases}$ d. $Polyglyceryl-3\ Methylglucose\ Distearate$ e. $\begin{cases} Sorbitan\ Stearate \\ Sucrose\ Cocoate \end{cases}$ f. $\begin{cases} Glyceryl\ Stearate \\ PEG-100\ Stearate \end{cases}$ g. $\begin{cases} Cetearyl\ Polyglucoside \\ Cetearyl\ Alcohol \end{cases}$ h. $\begin{cases} Ceteareth-4 \\ Ceteareth-10 \\ Ceteareth-20 \end{cases}$ These systems (a) to (h) have an average HLB value of about 10.

The mechanical strength can be increased by using the before mentioned hydrocolloids. Cholesterol is soluble in the liquid crystalline phase made of a variety of amphiphilic molecules and therefore an artificial membrane is formed that has similar properties as the naturally occurring subcutaneous membranes, and that is treated accordingly.

The emollients can be chosen from the emollients, which are used in personal care and cosmetic preparations, in a concentration in the range 0–45%, preferably in the range 5–20%. Examples of applicable emollients are triglycerides of long chain, predominantly unsaturated fatty acids such as vegetable oils and artificially made triglycerides of long chain unsaturated fatty acids, triglycerides of saturated medium chain fatty acids, liquid and semi-solid esters of mono- & polyhydric alcohols and carboxylic acids with 1–24 carbon atoms, liquid and semi-solid fatty alcohols & branched alcohols, their ethoxylates and propoxylates, liquid and semi-solid mineral and natural hydrocarbons, products having a steroid skeleton with an hydroxy functionality, their esters, ethoxylates and propoxylates, water-soluble products made by ethoxylation- and/or propoxylation of suitable mono- and/or -polyhydric alcohols and products usually identified as silicones such as cyclic and linear polydimethylsiloxanes and polyphenyltrimethylsiloxanes and derivates thereof made by ethoxylation and/or propoxylation.

The invention is explained in more detail with reference to the following examples and tanning tests carried out with different preparations.

EXAMPLE 1

An O/W lotion was prepared by mixing an oil phase and a water phase in a manner customary per se.

The oil phase used consisted of:

0.50 kg of phenoxyethanol (Phenonip, trade name, product of Nipa Industries, UK), 10.00 kg of an ester mixture, consisting of cetyl palmitate, octyl stearate and glyceryl stearate (Cetiol 868, product from Cognis), 6.00 kg of emulsifier mixture of ceteareth-20 and ceteareth-12 (Emulgade SE, product from Cognis), 2.00 kg of cetearyl alcohol (Lanette O, product from Cognis).

The water phase consisted of 76.50 kg of water and 5.00 kg of tanning mixture according to the invention, consisting of:

10 wt % of N-acetyltyrosine, 20 wt % of butylene glycol, 2 wt % of phytantriol, 3 wt % of hydrolysed vegetable protein, 3 wt % of polysorbate-20, 62 wt % of water.

EXAMPLE 2

In a manner known per se, a gel-type preparation was prepared by mixing a premix consisting of:

0.80 kg of thickener (Carbopol Ultrez 10 Polymer, B. F. Goodrich), and 12.90 kg of water, with a mixture consisting of:

0.80 kg of triethanolamine (Merck & Co.), and 0.50 kg of phenoxyethanol (Phenonip, Nipa Industries), and mixing the mixture thus obtained with a water phase consisting of 80.00 kg of water and 5.00 kg of the tanning mixture according to the invention described in Example 1.

EXAMPLE 3 (FOR COMPARISON)

An O/W lotion was formed in the same manner as in Example 1, and using the same substances and quantities, except that in the tanning mixture according to the invention the phytantriol used was replaced by adenosine triphosphate. A preparation of this type is disclosed by DE 37 32 154.

The preparations specified in the abovementioned examples were subjected to tests on human skin, using a tanning bed comprising 22 80-Watt lamps and a face tanner comprising 5 15-Watt lamps. The measuring equipment consisted of a melanin & erythema meter (Mexameter MX16 from Courage & Khazaka).

The duration of an insolation was 20 minutes.

The following results were obtained:

TABLE 1

| Measured tanning | Measurement number | | | | | | | | | |
|---|---|---|---|---|---|---|---|---|---|---|
| | 1 | 2 | 3 | 4 | 5 | 6 | 7 | 8 | 9 | 10 |
| Untreated skin (reference) | 447 | 430 | 451 | 445 | 436 | 436 | 445 | 443 | 440 | 430 |
| Test 1 (product of Example 3) | 461 | 452 | 456 | 458 | 548 | 455 | 453 | 463 | 461 | 457 |
| Test 2 (product of Example 1) | 484 | 518 | 498 | 510 | 502 | 512 | 509 | 520 | 518 | 526 |
| Test 3 (product of Example 2) | 543 | 542 | 544 | 536 | 563 | 545 | 546 | 539 | 548 | 544 |

These results are shown in the accompanying FIG. 1 and can be summarized as follows:

TABLE 2

| | Number of insolations | Average tanning | Percentage tanning based on reference |
|---|---|---|---|
| Untreated skin (reference) | 0 | 440 | 0% |
| Test 1 (product of Example 3) | 6 | 457 | 4% |
| Test 2 (product of Example 1) | 4 | 509 | 16% |
| Test 3 (product of Example 2) | 6 | 545 | 24% |

To summarize, it can be stated that after as little as 6 insolations using a product according to the invention, a significant difference of 20% can be seen compared with a known preparation. After as little as 4 insolations, incidentally, a difference of 12% is already visible, compared with the known preparation.

EXAMPLE 4

Moisturisation Using a Controlled Release Preparation

Emulsions were made, composed as described in table 3.

TABLE 3

Moisturising emulsions

| Ingredient | Emulsion 1 (% b.w.) | Emulsion 2 (% b.w.) | Emulsion 3 (% b.w.) |
|---|---|---|---|
| water phase | | | |
| Demineralised Water | 62.20 | 63.70 | 63.10 |
| Polyglyceryl-3-Methylglucose Distearate (emulsifying agent) | 4.50 | 4.50 | 4.50 |
| Glycerin (humectant) | 3.00 | 3.00 | 3.00 |
| Cholesterol | 0.90 | — | — |
| Xantan Gum (thickener) | 0.40 | — | 0.40 |
| DMDM Hydantoin (preservative) | 0.30 | 0.30 | 0.30 |
| Carbomer (rheological additive) | 0.20 | 0.20 | 0.20 |
| Acrylates/$C_{10-30}$ Alkyl Acrylates Crosspolymer (rheological additive) | 0.20 | — | 0.20 |

TABLE 3-continued

Moisturising emulsions

| Ingredient | Emulsion 1 (% b.w.) | Emulsion 2 (% b.w.) | Emulsion 3 (% b.w.) |
|---|---|---|---|
| Methylparaben (preservative) | 0.17 | 0.17 | 0.17 |
| Aminomethyl Propanol (neutralising agent for rheological additives) | 0.10 | 0.10 | 0.10 |
| oil phase | | | |
| Caprylic/Capric Triglyceride (= refined coconut oil; emollient) | 8.00 | 8.00 | 8.00 |
| Isopropyl Isostearate (emollient and spreading agent) | 2.50 | 2.50 | 2.50 |
| Propylparaben (oil-soluble preservative) | 0.03 | 0.03 | 0.03 |
| Moisteriser | | | |
| Demineralised Water | 15.00 | 15.00 | 15.00 |
| Sodium PCA | 1.00 | 1.00 | 1.00 |
| Glucose (Natural moisterising factor) | 0.60 | 0.60 | 0.60 |
| Urea | 0.40 | 0.40 | 0.40 |
| Sodium Lactate | 0.30 | 0.30 | 0.30 |
| Lactic Acid | 0.20 | 0.20 | 0.20 |

DMDM hydantoin=1, 3-bis- (hydroxymethyl)-5, 5-dimethylimidazolidine2,4-dione.

Isopropylisostearate is a spreading agent, which improves the spreadability of the preparation on the skin.

heological additives are additives, which influence the mechanical strenght of the liquid crystalline structure of the emulsion to be prepared.

Procedure: Polyglyceryl-3 methylglucose distearate and cholesterol are dissolved at 85–90 C in about 25% water until a hazy, viscous gel is obtained. The formation of the liquid crystalline gel is monitored by optical microscopy. The rheological additives are dispersed at room temperature in the remainder of the water and this mixture is added to the liquid crystalline gel, and heated o 65 C. Finally the preservatives and glycerin are added and the mixture is kept at 65 C. The oil phase is heated to 65 C and added slowly to the water phase. After the addition the mixture is homogenised @1500 rpm during 2 minutes, without stirring during the addition. The emulsion is stirred slowly with a planetary mixer while cooling gently. At 45–50 C the moisturiser is added.

The results of emulsion 1 were compared to a similar emulsion in absence of Cholesterol, Xanthan Gum and Acrylates/Clo-3o Alkyl Acrylates Crosspolymer, whereby the formed emulsion is stable but where the mechanical strength is greatly reduced: emulsion 2.

The results were also compared to a similar emulsion in absence of Cholesterol, whereby an emulsion is formed that is stable, with unusually high mechanical strength of the LC structure: emulsion 3.

The efficacy of this controlled release emulsion system was tested by means of Trans Epidermal Water Loss (TEWL) measurements using TEWAMETERO by COURAGE & KHAZAKA.

Figure 2:
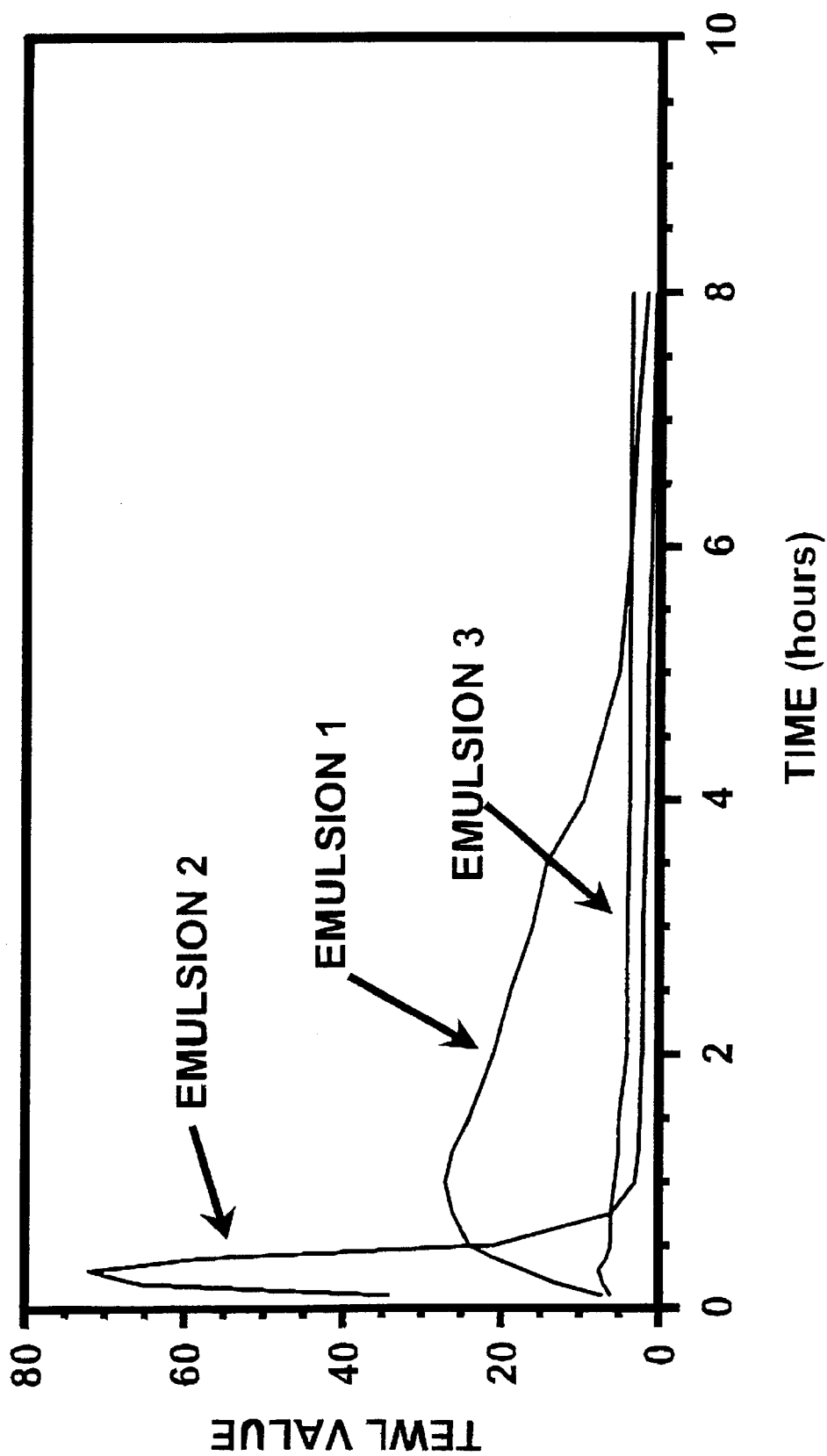

The results of the TEWL measurements are depicted in FIG. 2, which clearly demonstrates that the activity of emulsion 3 is unacceptable relative low in moisturising ability because of insufficient bio-availability of the moisturiser.

Emulsion 2 has a much too high bio-availability of the moisturiser, while the system (emulsion 1) with build-in controlled release has a highly desirable bio-availability profile.

EXAMPLE 5

Tanning acceleration using a controlled release tanning preparation according to the invention.

In typical experiments emulsions were made, composed as described in Tables 4 and 5, by following the procedure indicated in EXAMPLE 4.

TABLE 4

Tanning acceleration emulsions

| Ingredient | Emulsion $4^A$ (% b.w.) | Emulsion $5^A$ (% b.w.) | Emulsion $6^A$ (% b.w.) |
|---|---|---|---|
| water phase | | | |
| Demineralised Water | 29.84 | 31.64 | 31.04 |
| Polyglyceryl-3-Methylglucose Distearate (emulsifying agent) | 5.50 | 5.50 | 5.50 |
| Glycerin (humectant) | 3.00 | 3.00 | 3.00 |
| Cholesterol | 1.20 | — | — |
| Xantan Gum (thickener) | 0.40 | — | 0.40 |
| DMDM Hydantoin (preservative) | 0.30 | 0.30 | 0.30 |
| Carbomer (rheological additive) | 0.20 | 0.20 | 0.20 |
| Acrylates/$C_{10-30}$ Alkyl Acrylates Crosspolymer (rheological additive) | 0.20 | — | 0.20 |
| Methylparaben (preservative) | 0.17 | 0.17 | 0.17 |
| Aminomethyl Propanol (neutralising agent for rheological additives) | 0.10 | 0.10 | 0.10 |
| Trisodium EDTA | 0.05 | 0.05 | 0.05 |
| oil phase | | | |
| Paraffinum Liquidum | 6.00 | 6.00 | 6.00 |
| Homosalate | 5.00 | 5.00 | 5.0 |
| UV filter: Butyl Methoxydibenzoylmethane | 3.00 | 3.00 | 3.00 |
| Ethylhexyldodecanol (emollient) | 2.50 | 2.50 | 2.50 |
| Propylparaben (oil-soluble preservative) | 0.03 | 0.03 | 0.03 |
| tanning comp. | | | |
| Aloe Barbadensis (Aloe Vera Gel) (irritation quencher and emollient) | 40.00 | 40.00 | 40.00 |
| Butylene Glycol | 1.50 | 1.50 | 1.50 |
| Acetyl Tyrosine | 1.00 | 1.00 | 1.00 |
| Phytantriol | 0.01 | 0.010 | 0.01 |

Homosalate is added, as is well-known to improve the solubility of butyl methoxydibenzoylmethane. As butyl methoxydibenzoylmethane is a strong sequestering agent for transition metal ions the use of an additional sequestering agent such as trisodium ETDA is essential to avoid coloration of the final emulsion.

As an alternative other W filters can be used such as described in table 5: the use of octocrylene instead of butyl methoxydibenzoylmethane & homosalate.

TABLE 5

Tanning acceleration emulsions

| Ingredient | Emulsion $4^B$ (% b.w.) | Emulsion $5^B$ (% b.w.) | Emulsion $6^B$ (% b.w.) |
|---|---|---|---|
| water phase | | | |
| Demineralised Water | 31.84 | 33.64 | 33.04 |
| Polyglyceryl-3-Methylglucose Distearate (emulsifying agent) | 5.50 | 5.50 | 5.50 |
| Glycerin (humectant) | 3.00 | 3.00 | 3.00 |
| Cholesterol | 1.20 | — | — |
| Xantan Gum (thickener) | 0.40 | — | 0.40 |
| DMDM Hydantoin (preservative) | 0.30 | 0.30 | 0.30 |
| Carbomer (rheological additive) | 0.20 | 0.20 | 0.20 |
| Acrylates/$C_{10-30}$ Alkyl Acrylates Crosspolymer (rheological additive) | 0.20 | — | 0.20 |
| Methylparaben (preservative) | 0.17 | 0.17 | 0.17 |
| Aminomethyl Propanol (neutralising agent for rheological additives) | 0.10 | 0.10 | 0.10 |
| Trisodium EDTA | 0.05 | 0.05 | 0.05 |
| oil phase | | | |
| Paraffinum Liquidum | 6.00 | 6.00 | 6.00 |
| Octocrylene (UV filter) | 6.00 | 6.00 | 6.00 |
| Ethylhexyldodecanol (emollient) | 2.50 | 2.50 | 2.50 |
| Propylparaben (oil-soluble preservative) | 0.03 | 0.03 | 0.03 |
| tanning comp. | | | |
| Aloe Barbadensis (Aloe Vera Gel) (irritation quencher and emollient) | 40.00 | 40.00 | 40.00 |
| Butylene Glycol | 1.50 | 1.50 | 1.50 |
| Acetyl Tyrosine | 1.00 | 1.00 | 1.00 |
| Phytantriol | 0.01 | 0.01 | 0.01 |

The results of the emulsions $4^A/4^B$ were compared to similar emulsions in absence of Cholesterol, Xanthan Gum and Acrylates/$C_{10-30}$ Alkyl Acrylates Crosspolymer, whereby an emulsion is formed that is stable but where the mechanical strength is greatly reduced: emulsion $5^A/5^B$.

The results were also compared to a similar emulsions in absence of Cholesterol, whereby emulsions were formed, which are stable, but with unusually high mechanical strength of the LC structure: emulsion $6^A/6^B$.

The efficacy of this controlled release emulsion systems was tested by means of determination of melamin formation measurement using MEXAMETER by COURAGE & KHAZAKA.

It was found, that melanin formation during exposition to W-radiation was excellent for emulsion systems $4^A/4^B$. Obviously the bio-availability of the system Acetyl Tyrosine/Phytantriol is high. The MEXAMETER reading for emulsion $4^A$ was set at 100% as a reference. It was observed that the MEXAMETER reading from emulsion $4^B$ was 103%.

For emulsion $5^A/5^B$ the MEXAMETER readings were respectively 92% and 94%. Obviously the bio-availability for the emulsion systems $5^A/5^B$ is such that less functional material can be used for the production of melanin. The lower MEXAMETER readings for emulsions $5^A/5^B$ is attributed to the absence of a controlled release system using cholesterol. The reduced bio-availability of the active ingredients (Acetyl Tyrosine/Pythantriol) probably originates from a high trans-epidermal flux of the active ingredients disabling full utilisation thereof.

For emulsion $6^A/6^B$ the MEXAMETER readings were respectively 57% and 53%. Obviously the bio-availability of these emulsion systems is too low. The reduced bio-availability in this case is attributed to the fact that the emulsion system is much too stable and that insufficient material can be released.

The activity of the system Acetyl Tyrosine/Phytantriol can thus be further improved using controlled release systems based on amphiphilic products that form a liquid crystalline (LC) phase in the emulsion. The mechanical strength of the LC phase can be monitored using a suitable rheological additive.

Controlled release of active principles such as moisturisers or tanning accelerators can be monitored by incorporating cholesterol in the LC phase.

What is claimed is:

1. Tanning preparation for the skin comprising at least one tyrosine derivative of formula 1

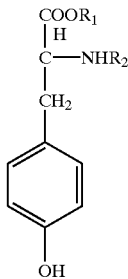

where $R^1$=—H,—$(CH_2)$ X—$CH_3$, x being an integer from 1 to 20, $R^2$=$CH_3CO$—, $CH_3$—$(CH_2)yCO$—, y being an integer from 1 to 20, and an activator, wherein the activator consists of an aliphatic polyol having at least 10 C atoms in the molecule.

2. Tanning preparation according to claim 1, wherein the aliphatic polyol consists of a hexadecanetriol, in particular phytantriol.

3. Tanning preparation according to claim 1, wherein said preparation comprises a tyrosine derivative of formula 1, where $R^1$, $R^2$, x and y have the abovementioned meanings and also comprises at least 0.01 wt % of phytantriol.

4. Tanning preparation according to claim 1, wherein the preparation further comprises riboflavin.

5. Tanning preparation according to claim 1, wherein the preparation further comprises a UV filter.

6. Tanning preparation according to claim 1, wherein the preparation is in a form selected from the group consisting of a gel, lotion, cream, foam, spray based on water, an aqueous alcohol, an aqueous glycol, or a combination thereof, or an emulsion of the type O/W, W/O, O/W/O.

7. Method of preparing a tanning preparation according to claim 1, wherein a mixture is formed which comprises 5–15 wt % of N-acetyl-L-tyrosine, 0.5–5 wt % of phytantriol, 15–25 wt % of butylene glycol, 1–5 wt % of hydrolysed vegetable protein, 0.1–5 wt % of polysorbate-20, 0–5 wt % of riboflavin, remainder: water/alcohol, and this mixture is taken up in an amount of from 1 to 10%, preferably 5%, in a pharmacologically acceptable base to form a preparation for topical application.

8. A controlled release tanning preparation for the skin comprising a stable emulsion containing a nematic liquid crystalline structure that is present in the continuous phase of the emulsion, based on self-assemblies of amphiphilic compounds, wherein said emulsion comprises a tanning preparation according to claim 1, and wherein the mechanical strength of said liquid crystalline structure is increased by means of a suitable hydrocolloid and/or a spacing compound.

9. A controlled release tanning preparation according to claim 8, wherein said hydrocolloid is a natural gum and said spacing compound is selected from the group consisting of saturated long chain fatty alcohols and mono- and diglycerides of fatty acids.

10. A controlled release tanning preparation according to claim 8, wherein said nematic liquid crystalline structure further comprises cholesterol.

* * * * *